United States Patent [19]

Wegner et al.

[11] Patent Number: 4,959,094
[45] Date of Patent: Sep. 25, 1990

[54] 1-CHLOROPYRIMIDINYL-1H-1,2,4-TRIAZOLE-3-SULPHONAMIDES AS HERBICIDES

[75] Inventors: Peter Wegner; Martin Krüger; Gerhard Johann; Reinhart Rusch; Richard Rees, all of Berlin, Fed. Rep. of Germany; John Head, Stortford; Graham Rowson, Hundon, both of England

[73] Assignee: Schering Aktiengesellschaft, Fed. Rep. of Germany

[21] Appl. No.: 340,484

[22] Filed: Apr. 19, 1989

[30] Foreign Application Priority Data

Apr. 20, 1988 [DE] Fed. Rep. of Germany ....... 3813885

[51] Int. Cl.$^5$ .................. C07D 403/04; C07D 409/14; A01N 43/54; A01N 43/653
[52] U.S. Cl. .......................................... 71/92; 71/90; 544/320; 544/321
[58] Field of Search ...................... 71/92, 90; 544/320, 544/321

Primary Examiner—John M. Ford
Attorney, Agent, or Firm—Ostrolenk, Faber, Gerb & Soffen

[57] ABSTRACT

The invention relates to new 1-chloropyrimidinyl-1H-1,2,4-triazol-3-sulphonamides of the general formual I

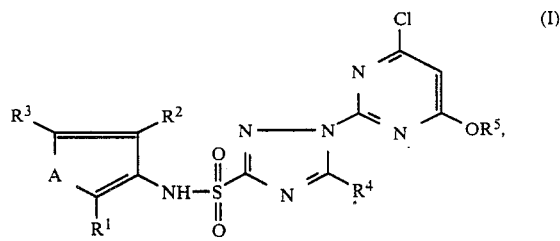

in which A, $R^1$, $R^2$, $R^3$, $R^4$ and $R^5$ have the meanings given in the description, processes for their preparation and their use as herbicides.

16 Claims, No Drawings

1-CHLOROPYRIMIDINYL-1H-1,2,4-TRIAZOLE-3-SULPHONAMIDES AS HERBICIDES

The invention relates to new 1-chloropyrimidinyl-1H-1,2,4-triazole-3-sulphonamides, processes for their preparation and their use as herbicides.

In EP Application 0 246 749 there are claimed herbicidal triazolesulphonamides of the formula:

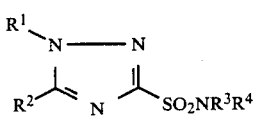

and salts thereof, where:
R$^1$ represents hydrogen, a substituted or unsubstituted alkyl, alkenyl, alkynyl, cycloalkyl, aryl, aralkyl, acyl, alkoxycarbonyl, aminocarbonyl or sulphonyl, or a heterocyclic group;
R$^2$ represents hydrogen, halo, cyano, hydroxy, mercapto, a substituted or unsubstituted alkyl, alkenyl, alkynyl, alkoxy, alkylthio, alkylsulphinyl, alkylsulphonyl, acyl, alkoxycarbonyl, aminocarbonyl, aryl or amino group, or a heterocyclic group;
R$^3$ represents a substituted or unsubstituted heterocyclic, benzheterocyclic, aryl or aralkyl group; and
R$^4$ represents hydrogen, a substituted or unsubstituted alkyl, alkenyl, alkynyl, acyl, alkylsulphonyl, alkoxycarbonyl, aminocarbonyl, aralkyl, or a group of the formula:

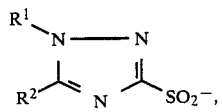

where R$^1$ and R$^2$ are as defined hereinbefore.

We have now found that a particular group of compounds within this broad claim have especially valuable properties. The selection of this group could not be predicted from the prior document nor could it be predicted that this group of compounds would show the particular advantages.

According to the invention there are provided 1-chloropyrimidinyl-1H-1,2,4-triazole-3-sulphonamides of the general formula I

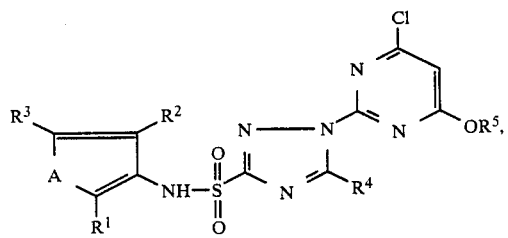

in which
A is —S— or —CH=CH—;
R$^1$ is halogen, methyl, trifluoromethyl, methoxy, difluoromethoxy, nitro or methoxycarbonyl;
R$^2$ is hydrogen, halogen, methyl, methoxy, allyloxy or propargyloxy;
R$^3$ is hydrogen or methyl;
R$^4$ is hydrogen, methyl or methoxymethyl; and
R$^5$ is C$_1$-C$_4$-alkyl.

The compounds of the invention are thus 1H-1,2,4-triazole-3-sulphonamide derivatives, carrying a phenyl or thienyl group (with defined substituents) on the sulphonamide linkage and in which the triazole is substituted in the 1-position by a 4-chloro-6-(C$_1$-C$_4$-alkoxy)-pyrimidin-2-yl group and substituted in the 5-position by hydrogen, methyl or methoxymethyl. In EP Application 0 246 749 there are no examples of any compounds containing a 1-(4-chloro-6-(C$_1$-C$_4$-alkoxy)-pyrimidin-2-yl) group. Further the only example of a compound comprising a thienyl group on the sulphonamide linkage has no substituents on the 1-position of the triazole group and is substituted at the 5-position by a pyrrole group.

The compounds of the invention are characterised by good herbicidal activity and especially high activity against Matricaria spp., combined with good crop selectivity, particularly in sugar beet. This combination of good Matricaria activity (which is a particularly important and difficult weed to control in sugar beet) combined with good sugar beet selectivity, is not generally seen in the compounds disclosed in EP Application 0 246 749.

The compounds of the invention of general formula I can be prepared for example by (A) reacting an amine of general formula II

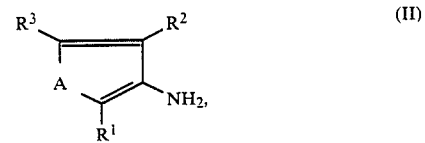

in which A, R$^1$, R$^2$ and R$^3$ have the meanings given above, with a sulphonylchloride of general formula III

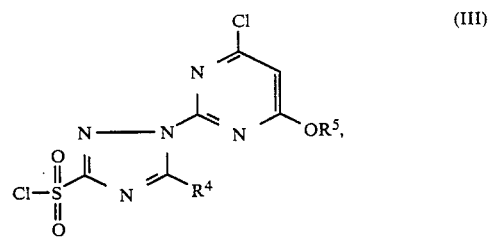

in which R$^4$ and R$^5$ have the meanings given above, in a suitable solvent and in the presence of an acid acceptor, or (B) reacting a compound of general formula IV

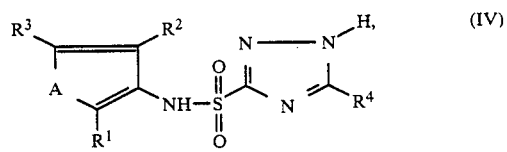

in which A, R$^1$, R$^2$, R$^3$ and R$^4$ have the meanings given above, with a compound of general formula V

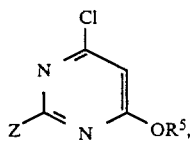

(V)

where Z is chlorine, bromine or an alkyl- or arylsulphonyl group and $R^5$ has the meaning given above, in a suitable solvent in the presence of an acid-binding agent.

The reaction variants are preferably carried out in the presence of a diluent. For this purpose there can be used solvents which are inert to the reactants.

Examples of such solvents or diluents are water, aliphatic, alicyclic and aromatic hydrocarbons, that can optionally be chlorinated, such as for example hexane, cyclohexane, petroleum ether, ligroin, benzene, toluene, xylene, methylene chloride, chloroform, carbon tetrachloride, ethylene dichloride and trichloroethane, ethers, such as for example diisopropyl ether, dibutyl ether, propylene oxide, dioxane and tetrahydrofuran, ketones, such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphones and sulphoxides, such as for example dimethyl sulphoxide and sulpholane, and bases, such as for example pyridine.

The reaction is suitably carried out between room temperature and the boiling point of the particular reaction mixture. The reaction can be carried out under atmospheric pressure but if desired higher or lower pressures can be used.

Process variant (A) is preferably carried out in chlorinated hydrocarbons, such as dichloromethane or dichloroethane, in the presence of a catalyst and/or acid acceptor. Examples of these are tertiary amines, such as for example triethylamine, diisopropylethylamine, N-methylmorpholine, 4-dimethylaminopyridine and pyridine. Pyridine can be used both as catalyst and as a solvent.

Process variant (B) is preferably carried out in inert solvents, such as dioxane, tetrahydrofuran, dimethylformamide or N-methylpyrrolidone, optionally in the presence of a catalyst. Examples of these are metal hydrides, tertiary amines, such as for example triethylamine or diisopropylethylamine and inorganic bases, such as for example alkali metal or alkaline earth metal hydroxides or carbonates.

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by fractionated distillation or crystallisation.

The compounds of the invention are, as a rule, colourless or odourless crystals that are slightly soluble in water and in aliphatic hydrocarbons, such as petroleum ether, hexane, pentane and cyclohexane, and highly soluble in halogenated hydrocarbons, such as chloroform, methylene chloride and carbon tetrachloride, aromatic hydrocarbons, such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of formula II, III, IV and V can be prepared as described in the literature and especially as described in EP Application 0 246 749.

As stated previously the compounds of the invention show good herbicidal activity. This activity is seen against monocotyledonous and dicotyledonous weeds with good selectivity in various crops as well as in sugar beet.

The compounds of the invention can be used for example against the following plant species:

Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.01 and 5 kg/ha.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added.

Herbicidally active mixing partners suitable in this connection include for example, the active agents listed in Weed Abstracts, Vol. 36, No. 12 (1987) under the heading "List of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitable be used, for example, as powders, dusts, granules, solutions, emulsios or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulphonate, polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

(A)

Wettable Powder (1)

25 percent by weight active ingredient
60 percent by weight kaolin
10 percent by weight silicic acid
5 percent by weight of a mixture of calcium ligninsulphonate and the sodium salt of N-methyl-N-oleyltaurine (2)

40 percent by weight active ingredient
25 percent by weight clay minerals
25 percent by weight silicic acid
10 percent by weight of a mixture of calcium lignosulphonate and alkylphenyl polyglycol ether (B)

Paste 45 percent by weight active ingredient
5 percent by weight sodium aluminium silicate
15 percent by weight cetyl polyglycol ether with 8 mol of ethylene oxide
2 percent by weight spindle oil
10 percent by weight polyethylene glycol
23 percent by weight water (C)

Emulsifiable Concentrate 25 percent by weight active ingredient
15 percent by weight cyclohexanone
55 percent by weight xylene
5 percent by weight of a mixture of calcium dodecylbenzenesulphonate and nonylphenolpolyoxyethylene.

The following examples illustrate the preparation of compounds according to the invention.

EXAMPLE 1

N-(2-Difluoromethoxy-6-methylphenyl)-1-(4-chloro-6-methoxypyrimidin-2-yl)-1H-1,2,4-triazole-3-sulphonamide 1.8 g (6 mmol) N-(2-Difluoromethoxy-6-methylphenyl)-1H-1,2,4-triazole-3-sulphonamide in 10 ml dimethylformamide was stirred with 1.68 g (12 mmol) potassium carbonate for 10 minutes at 50° C. It was then cooled to 10° C. and treated with 1.33 g (6 mmol) 4-chloro-6-methoxy-2-methylsulphonylpyrimidine and the mixture stirred for 45 minutes at 10° C. It was then added to ice-water, acidified to pH 4 with sulphuric acid and the solid collected and purified by silica gel chromatography using a mixture of methylene chloride and methanol (95/5).

Yield: 1.1 g=41% of theory.
M.p.: 215°–216° C.

In a similar manner to these processes the following compounds were prepared.

| Example | Name of Compound | Physical Constant |
| --- | --- | --- |
| 2 | N-(2,6-Difluorophenyl)-1-(4-chloro-6-methoxypyrimidin-2-yl)-1H-1,2,4-triazole-3-sulphonamide | mp: 229–234° C. |
| 3 | N-(2,6-Dichlorophenyl)-1-(4-chloro-6-methoxypyrimidin-2-yl)-1H-1,2,4-triazole-3-sulphonamide | mp: 235–240° C. |
| 4 | N-(2-Methoxycarbonyl-6-methylphenyl)-1-(4-chloro-6-methoxypyrimidin-2-yl)-1H-1,2,4-triazole-3-sulphonamide | mp: 147–152° C. |
| 5 | N-(2,6-Dichloro-3-methylphenyl)-1-(4-chloro-6-methoxypyrimidin-2-yl)-1H-1,2,4-triazole-3-sulphonamide | mp: 217–221° C. |
| 6 | N-(2-Chloro-6-methylphenyl)-1-(4-chloro-6-methoxypyrimidin-2-yl)-1H-1,2,4-triazole-3-sulphonamide | mp: 228–233° C. |
| 7 | N-(2,6-Dichloro-3-methylphenyl)-1-(4-chloro-6-ethoxypyrimidin-2-yl)-1H-1,2,4-triazole-3-sulphonamide | mp: 212–215° C. |
| 8 | N-(2-Trifluoromethylphenyl)-1-(4-chloro-6-methoxypyrimidin-2-yl)-1H-1,2,4-triazole-3-sulphonamide | mp: 191–194° C. |
| 9 | N-(2-Methoxyphenyl)-1-(4-chloro-6-methoxypyrimidin-2-yl)-1H-1,2,4-triazole-3-sulphonamide | mp: 175–178° C. |
| 10 | N-(2-Methoxycarbonyl-6-methyphenyl)-1-(4-chloro-6-ethoxypyrimidin-2-yl)-1H-1,2,4-triazole-3-sulphonamide | mp: 142–148° C. |
| 11 | N-(2-Methyl-6-nitrophenyl)-1-(4-chloro-6-methoxypyrimidin-2-yl)-1H-1,2,4-triazole-3-sulphonamide | mp: 221–224° C. |
| 12 | N-(2,6-Dichlorophenyl)-1-(4-chloro-6-ethoxypyrimidin-2-yl)-1H-1,2,4-triazole-1-sulphonamide | mp: 251–259° C. |
| 13 | N-(2,6-Difluorophenyl)-1-(4- | mp: 190–193° C. |

-continued

| Example | Name of Compound | Physical Constant |
|---|---|---|
| | chloro-6-ethoxypyrimidin-2-yl)-1H-1,2,4-triazole-3-sulphonamide | |
| 14 | N-(2,3-Dimethyl-6-nitrophenyl)-1-(4-chloro-6-methoxypyrimidin-2-yl)-1H-1,2,4-triazole-3-sulphonamide | mp: 226–230° C. |
| 15 | N-(2-Difluoromethoxy-6-methylphenyl)-1-(4-chloro-6-ethoxypyrimidin-2-yl)-1H-1,2,4-triazole-3-sulphonamide | mp: 147–150° C. |
| 16 | N-(2-Difluoromethoxyphenyl)-1-(4-chloro-6-methoxypyrimidin-2-yl)-1H-1,2,4-triazole-3-sulphonamide | mp: 178–181° C. |
| 17 | N-(2-Difluoromethoxyphenyl)-1-(4-chloro-6-ethoxypyrimidin-2-yl)-1H-1,2,4-triazole-3-sulphonamide | mp: 157–161° C. |
| 18 | N-(2,6-Dibromophenyl)-1-(4-chloro-6-methoxypyrimidin-2-yl)-1H-1,2,4-triazole-3-sulphonamide | mp: 266° C. (decomp) |
| 19 | N-(2-Allyloxy-6-nitrophenyl)-1-(4-chloro-6-methoxypyrimidin-2-yl)-1H-1,2,4-triazole-3-sulphonamide | mp: 173–176° C. |
| 20 | N-(2-Methoxy-6-nitrophenyl)-1-(4-chloro-6-methoxypyrimidin-2-yl)-1H-1,2,4-triazole-3-sulphonamide | mp: 222–225° C. |
| 21 | N-(2-Propargyloxy-6-nitrophenyl)-1-(4-chloro-6-methoxypyrimidin-2-yl)-1H-1,2,4-triazole-3-sulphonamide | mp: 176–180° C. |
| 22 | N-(2-Methoxy-6-nitrophenyl)-1-(4-chloro-6-ethoxypyrimidin-2-yl)-1H-1,2,4-triazole-3-sulphonamide | mp: 230–232° C. |
| 23 | N-(2-Allyloxy-6-nitrophenyl)-1-(4-chloro-6-ethoxypyrimidin-2-yl)-1H-1,2,4-triazole-3-sulphonamide | mp: 132–135° C. |
| 24 | N-(2-Propargyloxy-6-nitrophenyl)-1-(4-chloro-6-methoxypyrimidin-2-yl)-1H-1,2,4-triazole-3-sulphonamide | mp: 192–196° C. |
| 25 | N-(2,6-Dichloro-1-methylphenyl)-1-(4-chloro-6-n-propoxypyrimidin-2-yl)-1H-1,2,4-triazole-3-sulphonamide | mp: 197–199° C. |
| 26 | N-(2-Difluormethoxy-6-methylphenyl)-1-(4-chloro-6 -n-propoxypyrimidin-2-yl)-1H-1,2,4-triazole-1-sulphonamide | |
| 27 | N-(2-Allyloxy-6-nitrophenyl)-1-(4-chloro-6-n-propoxypyrimidin-2-yl)-1H-1,2,4-triazole-3-sulphonamide | mp: 164° C. |
| 28 | N-(2,6-Difluorophenyl)-1-(4-chloro-6-n-propoxypyrimidin-2-yl)-1H-1,2,4-triazole-3-sulphonamide | |
| 29 | N-(2-Methoxycarbonyl-6-methylphenyl)-1-(4-chloro-6-n-propoxypyrimidin-2-yl)-1H-1,2,4-triazole-3-sulphonamide | |
| 30 | N-(2-Methoxy-6-methoxycarbonylphenyl)-1-(4-chloro-6-n-propoxypyrimidin-2-yl)-1H-1,2,4-triazole-3-sulphonamide | mp: 166–167° C. |
| 31 | N-(2,6-Dichloro-3-methylphenyl)-1-(4-chloro-6-isopropoxypyrimidin-2-yl)-1H-1,2,4-triazole-3-sulphonamide | mp: 187° C. |
| 32 | N-(2-Difluoromethoxy-6-methylphenyl)-1-(4-chloro-6-isopropoxypyrimidin-2-yl)-1H-1,2,4-triazole-3-sulphonamide | |
| 33 | N-(2-Allyloxy-6-nitrophenyl)-1-(4-chloro-6-isopropoxypyrimidin-2-yl)-1H-1,2,4-triazole-3-sulphonamide | mp: 171–172° C. |
| 34 | N-(2,6-Difluorophenyl)-1-(4-chloro-6-isopropoxypyrimidin-2-yl)-1H-1,2,4-triazole-3-sulphonamide | |
| 35 | N-(2-Methoxycarbonyl-6-methylphenyl)-1-(4-chloro-6-isopropoxypyrimidin-2-yl)-1H-1,2,4-triazole-3-sulphonamide | |
| 36 | N-(2-Methoxy-6-methoxycarbonylphenyl)-1-(4-chloro-6-isopropoxypyrimidin-2-yl)-1H-1,2,4-triazole-3-sulphonamide | mp: 179–180° C. |
| 37 | N-(2-Methoxycarbonyl-4-methyl-3-thienyl)-1-(4-chloro-6-methoxypyrimidin-2-yl)-1H-1,2,4-triazole-3-sulphonamide | |
| 38 | N-(2-Methoxycarbonyl-4-methyl-3-thienyl)-1-(4-chloro-6-ethoxypyrimidin-2-yl)-1H-1,2,4-triazole-3-sulphonamide | |
| 39 | N-(2-Methoxy-6-methoxycarbonylphenyl)-1-(4-chloro-6-methoxypyrimidin-2-yl)-1H-1,2,4-triazole-3-sulphonamide | mp: 174–176° C. |
| 40 | N-(2,6-Difluorophenyl)-1-(4-chloro- | mp: 183–185° C. |

-continued

| Example | Name of Compound | Physical Constant |
|---|---|---|
|  | 6-methoxypyrimidin-2-yl)-5-methyl-1H-1,2,4-triazole-3-sulphonamide |  |
| 41 | N-(2,6-Dichlorophenyl)-1-(4-chloro-6-methoxypyrimidin-2-yl)-5-methyl-1H-1,2,4-triazole-3-sulphonamide | mp: 224–225° C. |
| 42 | N-(2,6-Dichloro-3-methylphenyl)-1-(4-chloro-6-methoxypyrimidin-2-yl)-5-methyl-1H-1,2,4-triazole-3-sulphonamide | mp: 214–215° C. |
| 43 | N-(2-Methyl-6-nitrophenyl)-1-(4-chloro-6-methoxypyrimidin-2-yl)-5-methyl-1H-1,2,4-triazole-3-sulphonamide | mp: 209–210° C. |
| 44 | N-(2,6-Difluorophenyl)-1-(4-chloro-6-methoxypyrimidin-2-yl)-5-methoxymethyl-1H-1,2,4-triazole-3-sulphonamide | mp: 185–186° C. |
| 45 | N-(2,6-Dichlorophenyl)-1-(4-chloro-6-methoxypyrimidin-2-yl)-5-methoxymethyl-1H-1,2,4-triazole-3-sulphonamide | mp: 193–195° C. |
| 46 | N-(2-Difluoromethoxy-6-methylphenyl)-1-(4-chloro-6-methoxypyrimidin-2-yl)-5-methyl-1H-1,2,4-triazole-3-sulphonamide | mp: 201–204°.C. |
| 47 | N-(2-Methoxycarbonyl-6-methylphenyl)-1-(4-chloro-6-methoxypyrimidin-2-yl)-5-methyl-1H-1,2,4-triazole-3-sulphonamide | mp: 162–165° C. |
| 48 | N-(2-Methoxycarbonyl-4-methyl-3-thienyl)-1-(4-chloro-6-methoxypyrimidin-2-yl)-5-methyl-1H-1,2,4-triazole-3-sulphonamide | mp: 162–165° C. |
| 49 | N-(2-Chloro-6-methoxycarbonylphenyl)-1-(4-chloro-6-methoxypyrimidin-2-yl)-5-methyl-1H-1,2,4-triazole-3-sulphonamide | mp: 191–193° C. |
| 50 | N-(2-Difluoromethoxy-6-methylphenyl)-1-(4-chloro-6-methoxypyrimidin-2-yl)-5-methoxymethyl-1H-1,2,4-triazole-3-sulphonamide | mp: 134–136° C. |
| 51 | N-(2-Methoxycarbonyl-4-methyl-3-thienyl)-1-(4-chloro-6-methoxypyrimidin-2-yl)-5-methoxymethyl-1H-1,2,4-triazole-3-sulphonamide | mp: 181–183° C. |
| 52 | N-(2-Methoxy-6-methoxycarbonylphenyl)-1-(4-chloro-6-methoxypyrimidin-2-yl)-5-methyl-1H-1,2,4-triazole-3-sulphonamide | mp: 212–213° C. |

The following examples illustrate the possibilities for use of the compounds of the invention.

EXAMPLE A

In a greenhouse, the noted plant species were treated pre-emergently with the noted compounds, at a rate of 0.03 kg active ingredient/ha. The compounds were sprayed evenly over the plants as emulsions in 500 liters water/ha. Three weeks after the treatment, the compounds of the invention showed a high crop selectivity in wheat as well as in typical succeeding cultures as sugar beets and rape with excellent activity against the weeds. The comparison materials did not show the similar high selectivity.

In the following table:
0 = no damage
4 = total destruction
— = not tested
TRZAX = *Triticum aestivum*
BEAVS = *Beta vulgaris*
BRSSS = Brassica sp.
MATCH = *Matricaria chamomilla.*

| Compounds of invention | TRAZAX | BEAVX | BRSSS | MATCH |
|---|---|---|---|---|
| Example 2 | 0 | 0 | 1 | 4 |
| Example 5 | 0 | 0 | 1 | 4 |
| Example 8 | 0 | 0 | 0 | 4 |
| Example 9 | 0 | 0 | 0 | 4 |
| Example 10 | 0 | 0 | 0 | 4 |
| Example 11 | 0 | 1 | 0 | 4 |
| Example 16 | 0 | 0 | 1 | 4 |
| Example 17 | 0 | 0 | 0 | 4 |
| Example 18 | 0 | 0 | 0 | 4 |
| Example 19 | 0 | 0 | 0 | 4 |
| Example 20 | 0 | 1 | 3 | 4 |
| Example 21 | 0 | 1 | 2 | 4 |
| Example 22 | 0 | 0 | — | 3 |
| Example 23 | 0 | 0 | — | 3 |
| Example 24 | 0 | 1 | — | 3 |
| Untreated Comparison | 0 | 0 | 0 | 0 |
| Thiameturon-methyl | 0 | 3 | 3 | 4 |
| Compound I 30 from EP Application 0 246 749 | — | 3 | — | 4 |
| Compound I 36 from EP Application 0 246 749 | — | 4 | — | 4 |

EXAMPLE B

In a greenhouse, the noted plant species were treated post-emergently with the noted compounds, at a rate of 0.03 kg active ingredient/ha. The compounds were sprayed evenly over the plants as emulsions in 500 liters water/ha. Two weeks after the treatment, the compounds of the invention showed a high crop selectivity in wheat as well as in typical succeeding cultures as sugar beets and rape as well as in cotton with excellent activity against the weeds. The comparison material did not show the similar high selectivity.

In the following table:
0 = no damage
4 = total destruction

— = not tested
TRZAX = *Triticum aestivum*
BEAVS = *Beta vulgaris*
BRSSS = Brassica sp.
GOSHI = *Gossypium hirsutum*
MATCH = *Matricaria chamomilla*.

| Compounds of invention | TRZAX | BEAVX | BRSSS | GOSHI | MATCH |
|---|---|---|---|---|---|
| Example 2 | 0 | 0 | 1 | 0 | 3 |
| Example 3 | 0 | 1 | 1 | 0 | 3 |
| Example 4 | 0 | 1 | 0 | 1 | 3 |
| Example 5 | 0 | 0 | 0 | 0 | 3 |
| Example 6 | 0 | 1 | 1 | 0 | 4 |
| Example 7 | 0 | 0 | 0 | 0 | 3 |
| Example 8 | 0 | 0 | 0 | 0 | 4 |
| Example 10 | 0 | 0 | 0 | 0 | 3 |
| Example 11 | 0 | 0 | 0 | 0 | 4 |
| Example 15 | 0 | 0 | — | 0 | 4 |
| Example 16 | 0 | 0 | 1 | 0 | 4 |
| Example 20 | 0 | 1 | 3 | 0 | 3 |
| Example 21 | 0 | 0 | 2 | 0 | 3 |
| Example 22 | 0 | 0 | — | 0 | 3 |
| Example 23 | 0 | 0 | — | 0 | 3 |
| Example 24 | 0 | 0 | — | 0 | 3 |
| Untreated Comparison | 0 | 0 | 0 | 0 | 0 |
| Thiameturon-methyl | 0 | 4 | 4 | 3 | 4 |

EXAMPLE C

In a greenhouse, the compounds of the invention were sprayed pre-emergently over pots with Matricaria of different origin and with sugar beet varieties. The amount of water corresponded to about 200 liters/ha. In the following table the plant growth, four weeks after the treatment, is given as a relative value of the fresh weight of the plants compared with untreated plants.

As the example shows the compounds of the invention are well compatible to sugar beets and have at the same time an excellent activity against camomile.

In the following table:
MATCH = *Matricaria chamomilla*
BEAVA = *Beta vulgaris* ssp. *vulgaris* var. *altissima*
BEAVC = *Beta vulgaris* ssp. *vulgaris* var. *crassa*

| Compounds of invention | Dose g active ingredient/ha | Fresh weight (relative to untreated) | | | |
|---|---|---|---|---|---|
| | | MATCH | MATCH (UK) | BEAVA | BEAVC |
| Example 3 | 3 | 9 | 6 | 98 | 98 |
| | 10 | 0 | 0 | 104 | 99 |
| Example 5 | 10 | 6 | 2 | 96 | 97 |
| | 30 | 0 | 0 | 101 | 95 |
| Example 8 | 10 | 0 | 0 | 99 | 99 |
| | 30 | 0 | 0 | 93 | 97 |
| | 100 | 0 | 0 | 98 | 192 |
| Example 19 | 30 | 0 | 0 | 104 | 97 |
| | 100 | 0 | 0 | 99 | 99 |
| Example 20 | 10 | 0 | 0 | 100 | 103 |
| Example 21 | 10 | 0 | 0 | 110 | 106 |
| Example 22 | 10 | 0 | 0 | 94 | 92 |
| | 30 | 0 | 0 | 98 | — |
| | 30 | 0 | 0 | 97 | — |
| Example 23 | 10 | 1 | 1 | 69 | 104 |
| | 30 | 0 | 0 | 100 | 107 |
| Example 24 | 10 | 0 | 0 | 94 | 107 |
| | 30 | 0 | 0 | 93 | 110 |
| Untreated Comparison | — | 100 | 100 | 100 | 100 |
| Ethofumesate | 500 | 107 | 78 | 89 | 96 |
| | 1000 | 88 | 82 | 74 | 100 |

EXAMPLE D

In a greenhouse, the compounds of the invention were sprayed post-emergently over pots with plants of Matricaria species and sugar beet varieties. The amount of water corresponded to about 200 liters/ha. Two weeks after the treatment, the fresh weight of the plants was dertermined and given in the following table as a relative value compared with untreated plants.

As the example shows the compounds of the invention are well compatible to sugar beets and have at the same time an excellent activity against camomile. The comparison material did not show the similar high activity.

In the following table:
MATCH = *Matricaria chamomilla*
MATIN = *Matricaria inodora*
MATMT = *Matricaria matricarioides*
BEAVA = *Beta vulgaris* ssp. *vulgaris* var. *altissima*
BEAVC = *Beta vulgaris* ssp. *vulgaris* var. crassa
BEAVD = *Beta vulgaris* ssp. *vulgaris* var. *conditiva*.

| Compounds of invention | Dose g active ingredient/ha | Fresh weight (relative to untreated) | | | | | | |
|---|---|---|---|---|---|---|---|---|
| | | MATCH | MATCH (UK) | MATIN | MATMT | BEAVA | BEAVC | BEAVD |
| Example 3 | 300 | 4 | 7 | 19 | 3 | 93 | 91 | 85 |
| Example 4 | 100 | 6 | 7 | 21 | 18 | 98 | 95 | 86 |
| | 300 | 3 | 5 | 9 | 7 | 95 | 95 | 81 |

-continued

| Compounds of invention | Dose g active ingredient/ha | MATCH | MATCH (UK) | MATIN | MATMT | BEAVA | BEAVC | BEAVD |
|---|---|---|---|---|---|---|---|---|
| Example 5 | 300 | 12 | 13 | 54 | 26 | 106 | 99 | 90 |
| Example 6 | 300 | 6 | 6 | 8 | 14 | 95 | 94 | 99 |
| Example 8 | 100 | 6 | 11 | 48 | 13 | 107 | 103 | 98 |
| Example 22 | 300 | 8 | 4 | 13 | 7 | 91 | 95 | 98 |
| Example 23 | 300 | 9 | 10 | 20 | 12 | 95 | 96 | 95 |
| Example 24 | 300 | 8 | 9 | 16 | 12 | 99 | 96 | 110 |
| Untreated Comparison | — | 100 | 100 | 100 | 100 | 100 | 100 | 100 |
| Phenmedipham | 320 | 46 | 49 | 50 | 26 | 104 | 130 | 105 |
|  | 960 | 18 | 23 | 20 | 12 | 98 | 93 | 90 |

Fresh weight (relative to untreated)

EXAMPLE E

In a greenhouse, the noted plant species were treated pre-emergently with the noted compounds of the invention, at the rate shown. The compounds of the invention were sprayed evenly over the vessels containing seeds of the plants as an aqueous acetone solution containing a wetting agent. After 3 to 4 weeks growth, the plants were visually assessed for any herbicidal response.

In the following table:
0 = no effect
1 = 1–24% effect
2 = 35–69% effect
3 = 70–89% effect
4 = 90–100% effect
— = not tested
GALAP = *Galium aparine*
MATIN = *Matricaria inodora*
MATCH = *Matricaria chamomila*
BEAVS = *Beta vulgaris*.

EXAMPLE F

In a greenhouse, seedlings of the noted plant species were treated post-emergently with the noted compounds of the invention, at the rate shown. The compounds of the invention were sprayed evenly over the vessels containing the plants as an aqueous acetone solution containing a wetting agent. After 3 to 4 weeks growth, the plants were visually assessed for any herbicidal response.

In the following table:
0 = no effect
1 = 1–24% effect
2 = 25–69% effect
3 = 70–89% effect
4 = 90–100% effect
— = not tested
GALAP = *Galium aparine*
MATIN = *Matricaria inodora*
MATCH = *Matricaria chamomila*

| Compounds of invention | kg active ingredient/ha | GALAP | MATIN | MATCH | BEAVS |
|---|---|---|---|---|---|
| Example 40 | 0.032 | 3 | 4 | — | 0 |
| Example 41 | 0.25 | 3 | — | — | 2 |
| Example 42 | 0.016 | 1 | 4 | 4 | 0 |
| Example 43 | 0.25 | 3 | — | — | 2 |
| Example 44 | 0.25 | 2 | — | — | 2 |
| Example 45 | 0.25 | 3 | — | — | 2 |
| Example 46 | 0.25 | 3 | — | — | 2 |
| Example 47 | 0.016 | 3 | 4 | 4 | 0 |
| Example 48 | 0.25 | 2 | 4 | 2 | 1 |
| Example 49 | 0.016 | 2 | 4 | 4 | 1 |
| Example 50 | 0.016 | — | 4 | 4 | 1 |
| Example 51 | 0.032 | 2 | 4 | — | 2 |
| Example 52 | 0.25 | 4 | — | — | — |
| Untreated | — | 0 | 0 | 0 | 0 |

BEAVS = *Beta vulgaris*.

| Compounds of invention | kg active ingredient/ha | GALAP | MATIN | MATCH | BEAVS |
|---|---|---|---|---|---|
| Example 40 | 0.016 | 3 | 4 | 4 | 2 |
| Example 41 | 0.25 | 4 | — | — | 2 |
| Example 42 | 0.125 | 3 | — | — | 1 |
| Example 43 | 0.25 | 2 | — | — | 2 |
| Example 44 | 0.25 | 2 | — | — | 2 |
| Example 45 | 0.016 | 2 | 4 | 4 | 0 |
| Example 46 | 0.25 | 4 | 3 | 3 | 2 |
| Example 47 | 0.25 | 3 | — | — | — |
| Example 49 | 0.125 | 4 | — | — | 2 |
| Example 50 | 0.125 | 4 | 4 | — | 2 |
| Example 52 | 0.125 | 4 | 4 | — | 2 |
| Untreated | — | 0 | 0 | 0 | 0 |

We claim:
1. 1-Chloropyrimidinyl-1H-1,2,4-triazole-3-sulphonamide of formula I

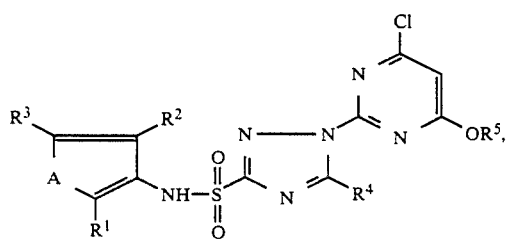

in which
A is —S— or —CH=CH—;
$R^1$ is halogen, methyl, trifluoromethyl, methoxy, difluoromethoxy, nitro or methoxycarbonyl;
$R^2$ is hydrogen, halogen, methyl, methoxy, allyloxy or propargyloxy;
$R^3$ is hydrogen or methyl;
$R^4$ is hydrogen, methyl or methoxymethyl; and
$R^5$ is $C_1$-$C_4$-alkyl.

2. A herbicidal composition which comprises a herbidically effective amount of a compound according to claim 1, in admixture with agriculturally acceptable carriers or diluents.

3. A method of combating weeds which comprises applying to the weeds or their locus a herbicidally effective amount of a compound according to claim 1.

4. A sulphonamide according to claim 1 in which
A is —CH=CH—;
$R^1$ is halogen, difluormethoxy or methoxycarbonyl,
$R^2$ is halogen or methyl,
$R^3$ is hydrogen or methyl,
$R^4$ is hydrogen and
$R^5$ is methyl.

5. A sulphonamide according to claim 4 in which $R^1$ is halogen.

6. A sulphonamide according to claim 4 in which $R^1$ is difluormethoxy.

7. A sulphonamide according to claim 4 in which $R^1$ is methoxycarbonyl.

8. The sulphonamide of claim 4 in which $R^2$ is halogen.

9. The sulphonamide of claim 4 in which $R^2$ is methyl.

10. The sulphonamide of claim 4 in which $R^3$ is halogen.

11. The sulphonamide of claim 4 in which $R^3$ is methyl.

12. N-(2,6-Dichloro-3-methylphenyl)-1-(4-chloro-6-methoxypyrimidin-2-yl)-1H-1,2,4-triazole-3-sulphonamide according to claim 2.

13. A herbicidal composition which comprises a herbidically effective amount of a compound according to claim 12, in admixture with agriculturally acceptable carriers or diluents.

14. A herbicidal composition which comprises a herbidically effective amount of a compound according to claim 4, in admixture with agriculturally acceptable carriers or diluents.

15. A method of combating weeds which comprises applying to the weeds or their locus a herbicidally effective amount of a compound according to claim 12.

16. A method of combating weeds which comprises applying to the weeds or their locus a herbicidally effective amount of a compound according to claim 4.

* * * * *